(12) United States Patent
Muchin

(10) Patent No.: US 6,241,998 B1
(45) Date of Patent: Jun. 5, 2001

(54) DERMATOLOGICAL PATCH

(75) Inventor: Jerome D. Muchin, Los Angeles, CA (US)

(73) Assignee: Acutek International, Inglewood, CA (US)

( * ) Notice: Subject to any disclaimer, the term of this patent is extended or adjusted under 35 U.S.C. 154(b) by 0 days.

(21) Appl. No.: 09/241,389

(22) Filed: Feb. 2, 1999

(51) Int. Cl.[7] .................................................. A61K 9/70
(52) U.S. Cl. .................................... 424/448; 424/448
(58) Field of Search ................... 424/443, 448; 514/859

(56) References Cited

U.S. PATENT DOCUMENTS

| | | |
|---|---|---|
| 3,499,446 | 3/1970 | Tsuneizumi et al. ............... 128/260 |
| 3,683,091 | 8/1972 | Nagata et al. . |
| 3,966,902 | 6/1976 | Chromecek . |
| 4,126,142 | 11/1978 | Saute . |
| 4,163,092 | 7/1979 | Steckler . |
| 4,532,937 | 8/1985 | Miller . |
| 4,556,441 | * 12/1985 | Faasse ................................. 156/247 |
| 4,581,402 | 4/1986 | Dunk et al. . |
| 4,619,826 | 10/1986 | Lay et al. . |
| 4,629,623 | 12/1986 | Balazs et al. . |
| 4,738,848 | 4/1988 | Yoshida et al. . |
| 4,879,361 | 11/1989 | Rehmer et al. . |
| 4,990,339 | 2/1991 | Scholl et al. . |
| 5,094,857 | 3/1992 | Luderschmidt . |
| 5,161,688 | 11/1992 | Muchin . |
| 5,208,016 | 5/1993 | Ohmae et al. . |
| 5,254,338 | 10/1993 | Sakai et al. . |
| 5,466,456 | 11/1995 | Glover ................................. 424/401 |
| 5,480,648 | 1/1996 | Wendel et al. . |
| 5,498,417 | 3/1996 | Lhila et al. . |
| 5,512,277 | 4/1996 | Uemura et al. . |
| 5,546,929 | 8/1996 | Muchin . |
| 5,573,778 | 11/1996 | Therriault et al. . |
| 5,662,923 | 9/1997 | Roreger . |
| 5,700,480 | 12/1997 | Hille et al. . |

FOREIGN PATENT DOCUMENTS

| | | | |
|---|---|---|---|
| 0 323 652 | 1/1988 | (EP) . | |
| 0 976 383 | 2/2000 | (EP) . | |
| 2 063 743 | 7/1971 | (FR) . | |
| 2 144 133 | 2/1985 | (GB) . | |
| 2318979 | * 5/1998 | (GB) | .............................. A61F/13/12 |
| 90/02774 | 3/1990 | (WO) . | |
| 97/32567 | * 9/1997 | (WO) | .............................. A61K/7/48 |

OTHER PUBLICATIONS

A. Julien and A. Pourrat (1986) "Les masques de beaute" Parfums, Cosmetiques, Aromes 72:61–64.
H. Toida (1980) "Pack Cosmetic" Hadashiyouhin Kagaku Kaihou Kenkyusho K.K., 4(186) (C–36) (668).
K. Shimizu (1988) "Pack Cosmetic" Shiseido Co. Ltd., 12(242) (C–510) (3089).
K. Ueda (1988) "Film–Forming Cosmetic Pack" Mikimoto Seiyaku K.K. 12(279) (C–517) (3126).

* cited by examiner

Primary Examiner—Thurman K. Page
Assistant Examiner—S. Howard
(74) Attorney, Agent, or Firm—Oppenheimer, Wolf, Donnelly LLP

(57) ABSTRACT

A dermatological patch for removing keratotic plugs from pores of the skin to improve the health and appearance of skin. The patch comprises a pad having a lower surface having a polymeric adhesive composition, which does not require premoisturization of the patch by the user to effect its operation. The patch can be of different shapes, formed of transparent, clear or colored material so as to enhance its cosmetic appearance on the skin, and contain additives to enhance the use of the patch for improving skin health.

22 Claims, 3 Drawing Sheets

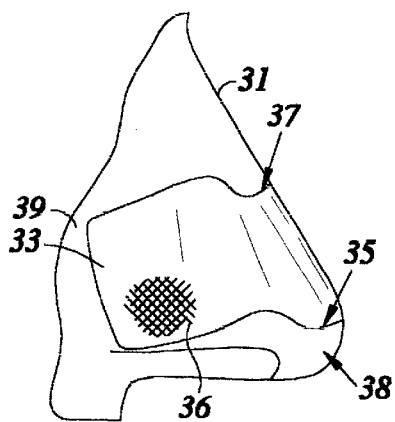
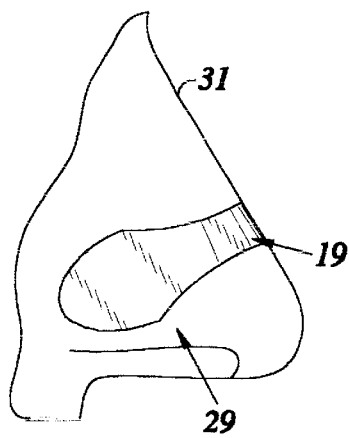
Fig. 3a    Fig. 3b
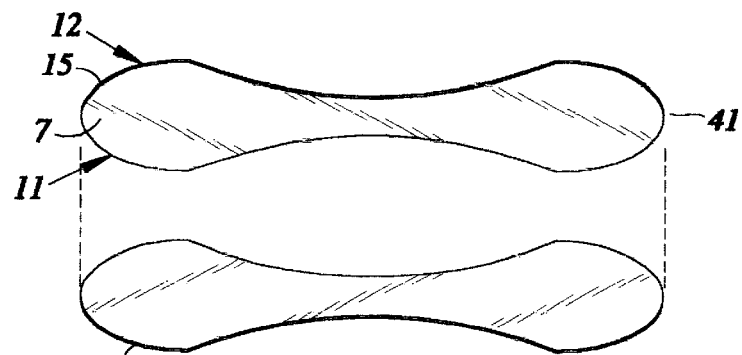
Fig. 4a
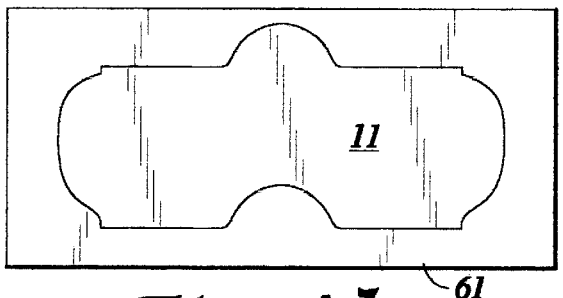
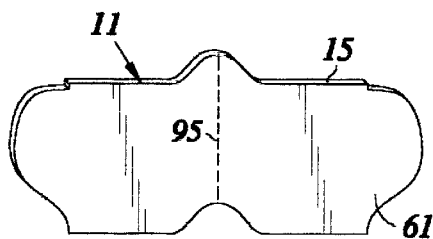
Fig. 4b    Fig. 4c

DERMATOLOGICAL PATCH

BACKGROUND OF THE INVENTION

This invention relates to a dermatological patch for the removal of keratotic plugs from human skin, and a method for the use of the dermatological patch. In particular, the invention is concerned with a dermatological patch having a polymeric adhesive composition, and a method of removing keratotic plugs from the skin utilizing such a dermatological patch.

Keratotic plugs are dead epidermal cells combined with sebaceous matter and dirt which form within skin pores, and result in conspicuously enlarged and/or darkened pores. If keratotic plugs are not periodically removed from the skin, not only do pores enlarge and darken, but further dermatological irritation may occur resulting in reddening blemishes or bacterial infections of the skin. Thus, removal of keratotic plugs improves the health and appearance of the skin.

A previously described method for removing keratotic plugs comprises applying a keratotic plug remover composition onto the skin, and peeling off the composition after the composition is dried. Use of a moistened composition may be awkward and uncomfortable for the user, and also the packaging of such a product is complex. The techniques and technology have been discussed in U.S. Pat. No. 5,512,277 (Uemura), which is incorporated by reference herein.

There is a need to provide a dermatological patch for the removal of keratotic plugs from the skin which minimizes the disadvantages of known systems.

SUMMARY OF THE INVENTION

The invention provides a dermatological patch which has advantages over known systems for removing keratotic plugs from the skin. There is also provided a method for removing keratotic plugs from the skin utilizing the dermatological patch.

According to the invention, there is provided a dermatological patch for removing keratotic plugs from the skin. The patch comprises a pad, having an upper and lower surface area, and a polymeric adhesive composition on the lower surface area of the pad for adhering to skin and removing keratotic plugs. The pad is a substrate which is preferably flexible and not microporus. The polymeric adhesive composition is preferably a pressure sensitive adhesive, and is selected to have a desired property of being in an active form once adhered to the pad. Premoisturization of the adhesive by a user prior to application onto the skin is not required to effect its operation.

Examples of polymeric adhesive compositions for coating the lower surface of the pad, include, but are not limited to pressure sensitive, acrylate adhesives. The adhesive operates based on its pressure sensitive characteristics, namely when applied to the skin, it can act, on removal from the skin, to remove the keratotic plugs from the skin, but not damage the skin.

In alternative embodiments, the patch can be made in a variety of shapes.

In some embodiments, the patch is used on non-hairy skin, such as the face. Examples of areas of the face upon which the patch may be used include, but are not limited to, the nose, cheeks, forehead and chin.

In a further embodiment, the patch additionally includes an additive agent.

In some embodiments, at least one of and preferably both of the pad and polymeric adhesive composition are substantially transparent or clear, a flesh-like color or shade so as to effectively blend with the skin of wearer, or translucent. In other embodiments, the pad is effectively colored or rendered ornate or patterned on its upper surface.

In one embodiment, the patch further includes a liner, secured to the patch by the adhesive, to cover the polymeric adhesive composition prior to use.

The invention also provides a method of use of the dermatological patch to remove keratotic plugs. The method comprises obtaining a dermatological patch, removing the liner to expose the adhesive surface of the patch, applying the patch to the skin with the lower surface of the pad to the skin, and removing the patch from the skin, thereby extracting the keratotic plugs from the skin. The relatively dry form of the adhesive does not require it to be premoistened before it is applied to the skin.

The invention is further described with reference to the accompanying drawings.

BRIEF DESCRIPTION OF THE DRAWINGS

FIG. 3a is a side view of an elongated, curvilinear rectangle-like shaped patch on the skin of the nose.

FIG. 3b is a side view of an hour-glass shaped patch on the skin of the nose.

FIG. 4a is an exploded perspective top view of the components making up the patch.

FIG. 4b is an exploded perspective top view of a second embodiment of the components making up the patch.

FIG. 4c is an exploded perspective top view of a second embodiment of the components making up the patch.

DETAILED DESCRIPTION OF THE PREFERRED EMBODIMENT

Figure 1:
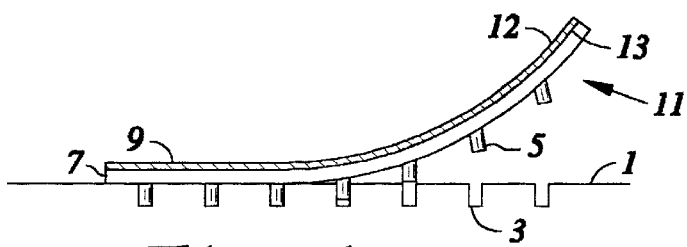
FIG. 1 is a side view of the patch being removed from the skin with adhered keratotic plugs.

A dermatological patch (patch) 11 removes keratotic plugs 5 upon application and removal of the patch 11 from the skin 1. The plugs would otherwise fill pores 3 in the surface of the skin 1.

Pad

The patch 11 includes a pad 9 having an upper surface area 12, a lower surface area 13 and a peripheral edge 15. There is also a layer 7 of pressure sensitive adhesive on the lower surface area 13 of the pad 9.

The pad material which is useful for this invention is not particularly limited as long as it can provide a suitable substrate for the polymeric adhesive composition and is sufficiently strong to withstand removal from the skin, having been secured to the skin by adhesive.

The pad material is preferably flexible, from the viewpoint of comfort, wherein flexibility is achievable by elasticity in any one or all axis of the material. Examples of flexible materials include, but are not limited to cotton cloth, rayon cloth, tetron cloth, nylon cloth. Further, pliability of the patch is preferable to accommodate skin contours, when applied to an area of skin having alterations in surface angles (for example around the nostril skin area). Further, the pad is preferably non-stretchable in the planar axis of the material.

The pad is preferably not of a woven material, and preferably has a primarily uniform surface. Where the pad is of a woven material, the material can be woven to achieve a variety of woven patterns on the surface. Examples of woven patterns, include, but are not limited to a squares, circles or diamonds on the upper and/or lower surface of the pad. Such woven patterns may result in either pad surfaces being primarily uniform or textured 36. Such texture may provide an enhanced substrate for the adherence of the adhesive to the pad, as well as improved effectiveness of the adhesive in removing keratotic plugs. The pad is preferably non-microporous.

When the pad material is microporous, the microporous film can be, but is not limited to, an open-celled microporous film which is a microporous polypropylene such as CELGRAD™ (Celanese Fibers Marketing Company). Other such materials can be substituted provided they posses similar necessary qualities: namely open-celled, microporous materials that are essentially hydrophobic. Suitable examples include, but are not limited to, nonwoven materials comprising fibers selected from the group consisting of polyester, polyether and polyolefin fibers or nonwoven pulp sheets impregnated with polyethelene.

Pad materials which are not flexible may take the form of plastic film sheets, for example as described in U.S. Pat. No. 5,512,277 (Uemura).

The pad material is also preferably of a thickness to provide sufficient strength to the pad, but also a thinness which will be comfortable to the wearer and pliable to contact all skin surfaces. The approximate thickness can vary between the range of, but is not limited to, about 0.01 to about 0.05 mm.

Adhesive

The patch 11 includes the pad 9 having a lower surface area 13 covered by a layer of polymeric adhesive composition (adhesive) 7. The adhesive 7 is located on the lower surface of the pad 13 such that the entire engaging surface of the pad wholly adheres with the skin. In some cases, the adhesive may not engage the entire lower surface. There could be spaces or blank areas in the lower surface 13 which has no adhesive. This could facilitate removal of the patch from the skin. The blank areas could be located at any suitable strategic location on the lower surface 13.

The polymeric adhesive composition is preferably a pressure sensitive polymeric adhesive. The adhesive can be selected to have a desired property of being in an active form once adhered to the pad, such that the adhesive need not be premoisturized by the user prior to application to the skin to effect its operation. Further, the adhesive need not dry to effectively remove keratotic plugs from the skin. The adhesive, further, preferably can include less than about 59% by weight of the composition of solvent, and most preferably includes less than about 29% by weight of the composition of solvent.

The adhesive is preferably efficient at removing keratotic plugs, but not damaging to the skin. The strength of adhesion between the skin and adhesive is preferably maximally efficient at removing keratotic plugs from the pores of skin, while adhesion is not so aggressive as to damage skin upon the removal of the patch. Further, the adhesive preferably has a relatively greater adherence to the pad than to the skin. There can be a desired range of adhesive strength for the adhesive in the present invention. The strength can vary relative to the selected pad material.

The thickness of the adhesive layer is preferably thick enough to afford suitable adhesion between the pad and the skin of the user so as to promote adhesion of the keratotic plugs to the adhesive. The approximate thickness can vary between, but is not limited to the range of, about 0.01 to about 0.05 mm. Where more adhesive is applied, the strength of the adhesive will be less.

In one embodiment, the adhesive comprises pressure-sensitive polymer. An example of a pressure-sensitive polymer, is, but is not limited to an acrylate adhesive.

In one embodiment, the adhesive consists essentially of high-molecular weight polymers. Examples of high-molecular weight polymers which are useful in the invention include, but are not limited to, the homopolymers and interpolymers derived from monomers selected from the $C_2$ to $C_{10}$ aliphatic esters of acrylic and methacrylic acid, $C_2$ to $C_{10}$ aliphatic vinyl ethers and esters, acrylamides, urethanes and the like. A terpolymer of 2-ethylehexyl acrylate, vinyl acetate and tert-butyl acrylamide has been found to be particularly suitable. One such suitable terpolymer has the foregoing monomeric components present in approximate ratios of 60:25:15.

As will be appreciated, the adhesive should be applied to the film in such a manner as to provide as uniform a coating as possible. While coating weights may vary widely, depending on the adhesive used, for example between about 15 and about 60 gm per square meter, coating weights of between about 15 and about 30 gm per square meter are preferred.

The efficacy of the polymeric adhesive composition is enhanced when a pigment is further incorporated together with the mentioned polymers. The pigment is not particularly limited, and both organic and inorganic pigments can be used. Examples of the inorganic pigments are, but are not limited to, zinc oxide, titanium oxide, silica, alumina, barium sulfate, zirconium oxide, calcium carbonate, calcium silicate, ceramics, hydroxyapatite, boron nitride, sericite, mica, talc, kaolin, montmorillonite, hectorite, saponite, black iron oxide, yellow iron oxide, red iron oxide, prussian blue, ultramarine, carbon black, pearlescent pigments. Examples of the organic pigments are, but are not limited to, silk powders, cellulose powders, poly(meth)acrylic ester resins, polyamide resins, polyolefin resins, polyimide resins, polyurethane resins, polyester resins, polyether resins, polyvinyl chloride resins, urea resins, polyformaldehyde resins, polycarbonate resins, polyvinylacetate resins, polyvinylidene chloride resins, polyacrylonitrile resins, polysulfone resins, polystyrene resins, polyurea resins, silicone resins, melamine resins, polytetrafluoroethylene resins, rake pigments and azo dyes.

The particle size of the pigments is from about 0.001 to 1000 micrometers, and preferably from about 0.01 to 500 micrometers. Particle size of less than 0.001 micrometer is not preferred because good dispersibility cannot be obtained. Particle size over 1000 micrometers is not preferred, either, because of an unfavorable sensation to the skin. The mentioned pigments can be used as a complex or a mixture of one or more, if desired. The amount of the pigment is from 0.1 to 70% by weight, preferably from 1 to 40% by weight based on the total weight of the preparation.

When an oil component is further incorporated together with the polymers, the polymeric adhesive composition of this invention can achieve excellent removal of keratotic plugs without giving irritation to the skin. This is because the strength of the film at which it breaks upon peeling-off can be controlled by the oil component.

The oil component which is useful in this invention is a glycerol derivative represented by formula (I):

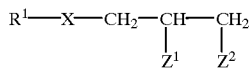

(I) wherein one of $Z^1$ and $Z^2$ represents $R^2$—Y— and the other represents a hydroxyl group or $R^3$—Y—, and $R^1$, $R^2$ and $R^3$ independently represent a hydrocarbon group, the total carbon number of which ranges from 13 to 40, and the hydrocarbon group may or may not be substituted by a silicone residual group, X and Y independently represent an oxygen atom or a group —COO—, (a carboxyl group in which the C atom is bonded to $R^1$, $R^2$, or $R^3$). Other oily ingredients which are generally incorporated into cosmetic preparations can also be used. Examples of the oil components which are useful in this invention include, but are not limited to, vegetable oils such as avocado oil, tsubaki oil, macadamia nut oil, olive oil and jojoba oil; animal oils and fats such as beef tallow, lard and egg yolk fat; aliphatic acids such as oleic acid and isostearic acid; alcohols such as hexadecyl alcohol and oleyl alcohol; esters such as cetyl 2-ethylhexanoate, 2-ethylhexyl palmitate, 2-octyldodecyl myristate, neopentyl glycol di-2-ethyl hexanoate, 2-octyldodecyl oleate, isopropyl myristate, glycerol triisostearate, mono-2-ethylhexanoic glyceryl diparamethoxycinnamate; and hydrocarbons such as dimethylpolysiloxane, dimethyl cyclopolysiloxane, methylphenyl polysiloxane, methylhydrogen polysiloxane, octamethyl cyclotetrasiloxane, octamethyl cyclopentasiloxane, decamethylcyclopentasiloxane, liquid paraffin, squalane, vaseline and solid paraffin.

Among these oil components, glycerol derivatives of formula (1) which are liquid at 20° C. are preferred, and particularly, tri-2-ethylhexanoic glycerol, 1-isostearoyl-3-myristoyl glycerol, 2-ethylhexanoic diglyceride, 1-hexyl-3-undecamethylhexasiloxy propynyl glycerol are most preferred.

The amount of the oil components to be incorporated into the keratotic plug remover of this invention is from about 0.5 to 30% by weight, preferably, about 1 to 15% by weight based on the total weight of composition.

Additives

The polymeric adhesive composition can further contain optional ingredients which are generally incorporated into cosmetic preparations. Examples of such optional ingredients include, but are not limited to, ethylene glycol, diethylene glycol, triethylene glycol and higher polyethylene glycols; propylene glycol, dipropylene glycol and higher polypropylene glycols, 1,3-butylene glycol, 1,4-butylene glycol and other butylene glycols; glycerol, diglycerol and higher polyglycerols; sugaralcohols such as sorbitol, mannitol, xylitol and maltitol; ethylene oxides (hereinafter referred to as EO) such as glycerols; addition products of propylene oxide (hereinafter referred to as PO); EO or PO adducts of sugaralcohols; monosaccharides such as galactose, glucose and fructose, and their EO or PO adducts; polysaccharides such as maltose and lactose, and their EO or PO adducts (polyols); surfactants such as POE alkyl ethers (POE is polyoxyethylene), POE branched alkyl ethers, POE sorbitan esters, POE glycerol fatty acid esters, POE hydrogenated castor oil, sorbitan ester, glycerol fatty acid esters and polyglycerol fatty acid ester; drugs such as vitamins, antiphlogistics, activators, UV absorbers and the like; water-swelling clay minerals such as montmorillonite, saponite and hectorite; polysaccharides such as carageenan, xanthangum, sodium alginate, pullulan, methylcellulose, carboxymethylcellulose, hydroxyethylcellulose and hydroxypropylcellulose; synthetic polymers such as carboxyvinyl polymers, polyvinyl pyrrolidones and polyvinyl alcohols. They are incorporated into the preparation of the present invention in such amounts that will not impede the effects of the invention. In particular, when polyols are used, they are preferably incorporated by 0.01 to 50% by weight based on the total preparation.

In some embodiments, other additives may be applied to the pad, or the polymeric adhesive composition or both. Additives can improve the attractiveness of the patch for marketing to a particular group of consumers, enhance the setting in which it is used, for example a spa environment, or enhance the ultimate goal of skin care by providing additional substances which are beneficial to the skin. Examples of additives include, but are not limited to fragrances or skin enhancers. Fragrances can be, but are not limited to men's or women's perfumes or plant extracts (fruit scents, floral scents, herbal scents (mint, eucalyptus)). Skin enhancers can be, but are not limited to antiseptics, antibacterials, moisturizers, such as aloe or vitamin E, detoxifiers, such as witchazel, free radical reducers, such as α-hydroxy or medications, such as retin A, benzoilperoxide or salicylic acid.

Shapes

Figure 2A:
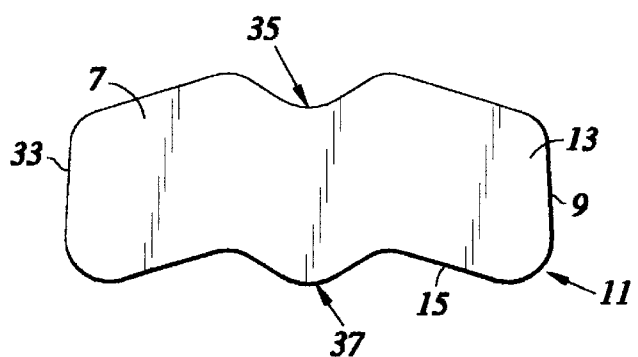
FIG. 2a is an underview of the patch showing adhesive on an elongated, curvilinear rectangle-like shaped patch.

The patch can be of different shapes and sizes for use on different locations of the skin, so as to most effectively adhere to the contours of the skin surface upon which it is used. In one embodiment, the patch comprises an elongated, curvilinear, rectangular-like shape (FIG. 2a). The patch 11 is an elongated element with end areas 33, where the peripheral edge 15 of the patch 11 defines a uniform width having an central portion with an indentation 35 on one side of the patch and a protrusion 37 on the opposite side, where the end area is approximately at least twice the area of the central portion. This shape is preferably, but not exclusively for use on the nose. The indented portion is substantially for location over the bridge 31 of the nose and the protrusion for location over the central portion of the nose 38, and the end areas are substantially for location over the sides of the nose as they transition into the cheek area 39 (FIG. 3a).

Figure 2B:
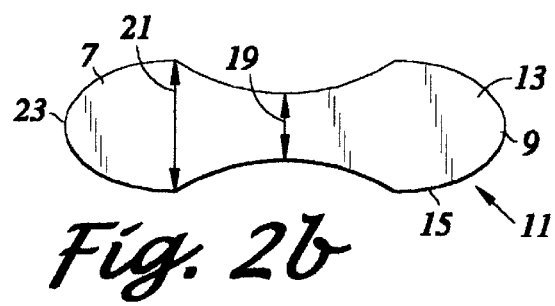
FIG. 2b is an underview of the patch showing adhesive on an hour-glass shaped patch.

In an alternative embodiment, the patch comprises an hour-glass shape (FIG. 2b). The patch 11 is an elongated element with rounded ends 23, where the peripheral edge 15 of the patch 11 defines a narrow width 19 and a broad width 21, where the end area of the broad width is approximately at least twice the area of the center region having a narrow width. This shape is preferably, but not exclusively for use on the nose. The narrow width 19 is substantially for location over the bridge 31 of the nose, and the broad width 21 is substantially for location centrally over the nostril outer skin 29 (FIG. 3b).

Figure 2C:
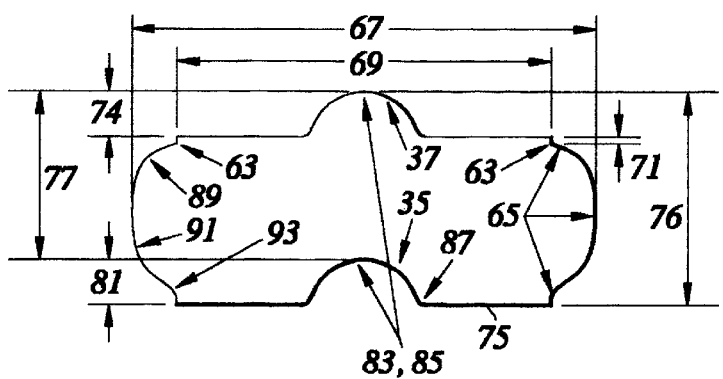
FIG. 2c is an underview of the patch showing adhesive on a butterfly shaped patch.

In an alternative embodiment, the patch comprises a butterfly shape (FIG. 2c). The patch 11 is an elongated element where the peripheral edge 15 of the patch 11 defines an indentation 35 on the lower side of the patch and a protrusion 37 on the upper side of the patch, notches 63 on the upper side of the patch, curvilinear end areas 65 where the end areas are approximately at least twice the area of the central portion containing the indentation and protrusion. One example of the dimensions of this embodiment include, but are not limited to the following. The total length of the patch 67 is about 3.150 inches; the length of the patch between notches 69 is about 2.3656 inches. The width of each notch 71 is about 0.0350 inches; the total width 73 of the patch from the lower side perimeter 75 to the upper most portion of the protrusion on the upper side 76 is about 1.3980 inches; the width between the upper most portion of the protrusion and the upper most portion of the indention 77 is about 1.1700 inches. The width between the upper most portion of the protrusion and the upper most portion of the notch 79 is about 0.2310 inches; the width between the upper most portion of the indention and the lower side perimeter 81 is about 0.2285 inches. The radius of curvature of the protrusion 83 and indention 85 are about 0.3128; the radius of curvature of the perimeter transition between the indention and the lower side perimeter 87 is about 0.1875. The radii of curvature of the perimeter of the curvilinear end areas are about 0.3533 89, about 0.5900 91 and about 0.3767 93, from the upper side to the lower side, respectively. The butterfly shape is preferably, but not exclusively for use on the nose. The indented portion is substantially for location over the bridge 31 of the nose and the protrusion for location over the central portion of the nose 38, and the end areas are substantially for location over the sides of the nose as they transition into the cheek area 39.

In further embodiments, the patch can be formed of a variety of different shapes. Examples of the shapes of the pad include, but are not limited to a triangle, square, rectangle, circle or oval. Such shapes may be suitable for use on different regions of the face, for example the nose, forehead, cheeks, and chin.

Use of the patch, however, is not limited to the face, but rather any skin surface upon which keratotic plugs have formed. The skin is preferably in a non-hairy skin region, as the adhesive which has a high affinity for the plugs is likely to also adhere to hairs, resulting in increased pain upon removal of the strip.

Color

In some embodiments, the pad material, adhesive, or both are substantially transparent, clear or colored, for instance, to conform to a flesh color or tone. In other embodiments, the upper surface of the pad 12 can be colored or rendered ornate or patterned by using different colors, patterns, shapes, words, or letters. Thus, when worn on the skin 1, there is the appearance of a colored device.

Liner

In some embodiments, the patch 11 includes a liner 61, for backing the pad 9 coated with the adhesive 7 prior to use. The liner is located on the lower surface area of the pad 13, such that the entire engaging surface adhesive is covered from exposure prior to use (FIG. 4a).

The liner is preferably bleached Kraft-Glassine paper, silicone coated on both sides. The liner is preferably designed to facilitate removal of the liner from the patch by the user. For example, the liner can be of the same dimensions as the patch, or may be of different dimensions than the patch to facilitate removal of the liner from the patch. Where the liner is of different dimensions as the patch, the liner can be larger in any one or all planar dimensions than the patch (FIG. 4b). Further, either where the liner is of the same dimensions or different dimensions than the patch, the liner may be scored or perforated 95 so as to facilitate removal of the liner from the patch (FIG. 4c).

USING THE DERMATOLOGICAL PATCH

The method of removing keratotic plugs using the dermatological patch comprises obtaining the patch, removing the liner to expose the adhesive surface of the patch, applying the patch to the skin having keratotic plugs with the lower surface of the pad to the skin, such that the adhesive is in direct contact with the skin. The user then waits a prescribed amount of time, such that the adhesive composition can bond to the keratotic plugs, and the patch is removed from the skin by lifting the perimeter of the patch to separate the patch from the skin, followed by pulling the entire patch from the skin, thereby removing the keratotic plugs from the pores of the skin after a predetermined period of time has elapsed (FIG. 1). When the keratotic plugs are removed from the skin, the health and appearance of the skin is improved.

MANUFACTURING THE PATCH

Figure 5A:
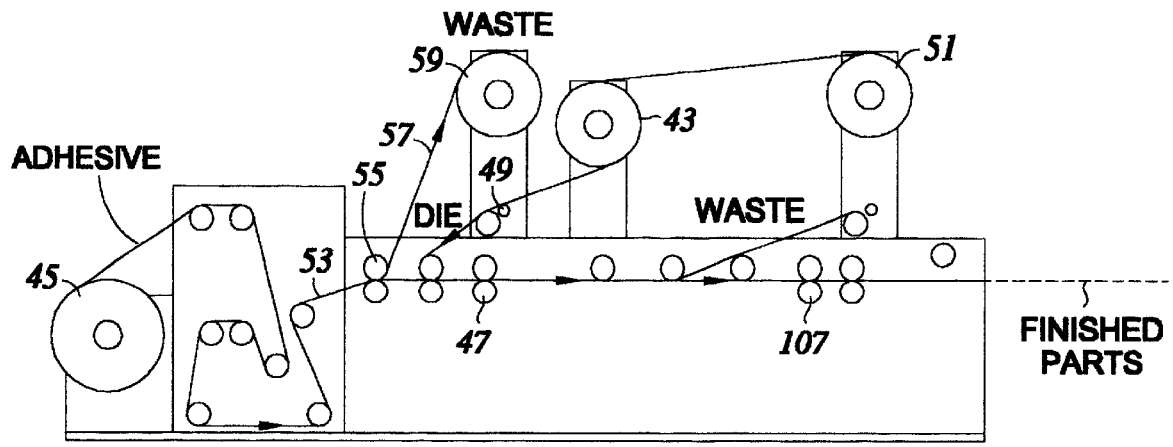
FIG. 5a is a diagrammatic view of a construction procedure for manufacturing the patch.

The method of manufacturing for the patch 11 requires the materials: pad 9, and adhesive 7, provided on rolls 43 and 45 of material, respectively (FIG. 5a).

The pad 9 is die cut at 47 from a ribbon 49 of pad material. The temporary liner is removed from the pad 9 to the waste liner roll 51.

Figure 5B:
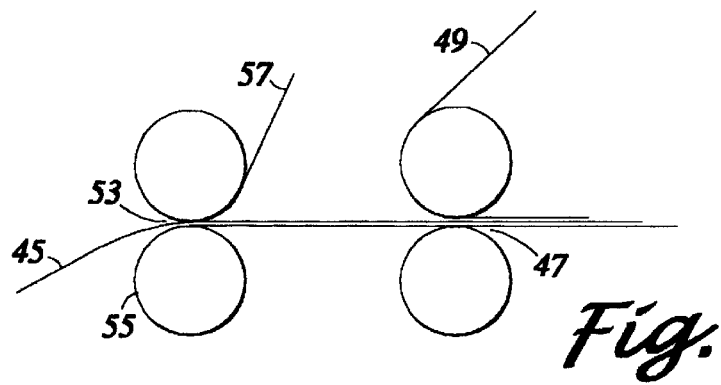
FIG. 5b is a side view of the patch respectively at two different die positions in the construction procedure.

The pad material and adhesive material are joined together in a webbing operation. The adhesive material 45, in the form of a second ribbon 53, is fed into a position at die 55 on one side of the pad material so as to place an adhesive material on the pad (FIG. 5b). The adhesive material 45 is cut at die 47 to conform with the pad. Non-adhering materials are removed as ribbons 57 of waste material onto a roll 59.

A liner 61 is also provided to cover the adhesive 7 of the patch 11. When in use, the liner 61 is removed to expose the adhesive surface 7. The liner 61 is formed as the base of the roll of material 45 for the adhesive ribbon 53.

Multiple patches 11 are formed in a nested series in the manufacturing process through dies 45 and 57. They are then cut and separated prior to packaging.

Figure 5C:
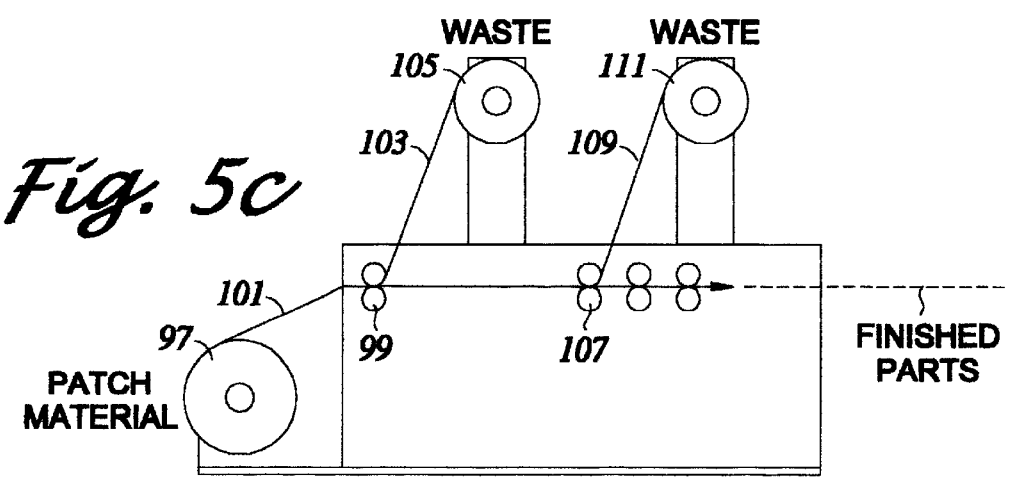
FIG. 5c is a diagrammatic view of an alternative construction procedure for manufacturing the patch.

In an alternative method of manufacturing of the patch 11, the patch material is provided on a roll 97, wherein the adhesive composition is pre-adhered to the lower surface of the pad material, and the liner is pre-adhered to the adhesive composition (FIG. 5c). The patch 11 is kiss-cut at 99 from a ribbon 101 of pad material, such that the pad 9 and adhesive 7 are formed in the shape of the patch 11. Non-adhering materials are removed as ribbons 103 of waste material onto a roll 105. The liner 61 is die cut at 107, and excess materials are removed as ribbons 109 onto roll 111.

GENERAL

Many other forms of the invention exist, each differing from others in matters of detail only.

In some cases, the dermatological patch may be used in addition to, or in place of removing keratotic plugs from the skin, to locally deliver agents which are beneficial to the skin.

In other situations, the dermatological patch may be used in addition to, or in place of removing keratotic plugs from the skin, to exfoliate dead skin cells from the skin.

Finally, the dermatological patch may be used in addition to, or in place of removing keratotic plugs from the skin, to locally deliver agents which are beneficial to the skin, as well as to exfoliate the skin.

The invention is to be determined solely in terms of the following claims.

What is claimed is:

1. A dermatological patch comprising a pad having a lower surface area and a polymeric adhesive composition adhered to the lower surface area of the pad, wherein the adhesive need not be premoisturized by the user prior to application to the skin, and wherein the adhesive engages the keratotic plug and is active in the physical removal of keratotic plugs from the skin, the keratotic plug consisting of dead epidermal cells formed within skin pores and being normally a non-fluid, and the physical removal of the plug being effected by engagement of the plug with the adhesive such that the plug does not engage the pad.

2. A dermatological patch for the removal of keratotic plugs from the skin, the keratotic plugs being dead epidermal cells formed within skin pores and being normally non-fluid, the patch comprising:

a pad having an upper and lower surface area, wherein the lower surface area includes a pressure sensitive adhesive composition for adhering to skin and wherein the pressure sensitive adhesive engages the keratotic plugs for removal of keratotic plugs from the skin; and the arrangement being such that when the patch is located on the skin, the surface of the patch with the pressure sensitive adhesive adheres to the skin and wherein the pressure sensitive adhesive engages the heads of the keratotic plugs to physically effect the removal of keratotic plugs from the skin when the patch is removed from the skin but not before the patch is removed from the skin.

3. A dermatological patch for the removal of keratotic plugs from the skin which comprises a flexible pad, the pad being relatively non-microporous and having adhered to its lower surface, a pressure sensitive adhesive composition, the pressure sensitive adhesive composition being sufficiently thick and continuous to hold the patch in close proximity with the skin and keratotic plugs, the pressure sensitive adhesive composition not requiring the application of moisture to be effective in adhering to the skin or keratotic plugs, nor requiring the drying of the pressure sensitive adhesive composition to effectively remove the keratotic plugs when the patch is removed from the skin, and wherein the pressure sensitive adhesive composition engages the keratotic plugs to effect the removal of keratotic plugs from the skin by withdrawing the plugs from pores when the patch is removed from adherence to the skin.

4. The dermatological patch as claimed in any one of claims 1, 2 or 3, wherein the pad is coated on one side with an adhesive such that when the patch is located on the skin of a user the adhesive contacts the skin and keratotic plugs in the skin.

5. The dermatological patch as claimed in any one of claims 1, 2 or 3, where the pad is formed by a non-stretchable material.

6. The dermatological patch as claimed in any one of claims 1, 2 or 3, where the pad is formed by at least one of a cotton cloth, rayon cloth, tetron cloth, nylon cloth or plastic film.

7. The dermatological patch as claimed in claim 1, where the polymeric adhesive composition includes a pressure sensitive adhesive.

8. The dermatological patch as claimed in any one of claims 1, 2 or 3, where the adhesive composition comprises an acrylate adhesive.

9. The dermatological patch as claimed in any one of claims 1, 2 or 3, where the adhesive composition includes at least one of a solvent, pigment or oil.

10. The dermatological patch as claimed in any one of claims 1, 2 or 3, wherein the pad or adhesive composition further includes an additive.

11. The dermatological patch as claimed in any one of claims 1, 2 or 3, wherein the pad and the adhesive composition further include an additive.

12. The dermatological patch as claimed in any one of claims 1, 2 or 3, where the pad or the adhesive composition is formed from a translucent or clear color material.

13. The dermatological patch as claimed in any one of claims 1, 2 or 3, where the pad and the adhesive composition are formed from a translucent or clear color material.

14. The dermatological patch as claimed in any one of claims 1, 2 or 3, where the pad or the adhesive composition is formed by at least partly translucent or clear color material.

15. The dermatological patch as claimed in any one of claims 1, 2 or 3, where the pad and the adhesive composition are formed by at least partly translucent or clear color materials.

16. The dermatological patch as claimed in any one of claims 1, 2 or 3, where the pad or the adhesive composition is formed by a flesh color material.

17. The dermatological patch as claimed in any one of claims 1, 2 or 3, where the pad and the adhesive composition are formed by a flesh color material.

18. The dermatological patch as claimed in any one of claims 1, 2 or 3, where the patch includes a liner adhered to the patch by the adhesive composition and removable from the pad.

19. The dermatological patch as claimed in any one of claims 1, 2 or 3, wherein the pad is formed of a material die cut from a first ribbon, and the adhesive composition is die cut from a second ribbon, and the ribbons are adhesively joined together, and wherein non-adhering materials removed from the die cuts are removed as ribbons of waste material.

20. A method for using a dermatological patch for the physical withdrawal of keratotic plugs from skin of a user, the keratotic plugs being essentially non-liquid cells located in pores of the skin, comprising:

(a) removing a liner from a dermatological patch, the liner having been secured by a pressure sensitive adhesive to the dermatological patch prior to use, and the dermatological patch consisting of a pad and a pressure sensitive adhesive, (b) applying the pressure sensitive adhesive coated surface of the patch to the skin having keratotic plugs, such that the pressure sensitive adhesive is in direct contact with the skin and the keratotic plugs, and without applying additional moisture to the patch to activate the pressure sensitive adhesive, and (c) physically removing the dermatological patch from the skin, whereby the pressure sensitive adhesive engaging with the keratotic plugs is active in the simultaneous physical removal of keratotic plugs from the skin by withdrawing the plugs from the pores, and not wherein such withdrawal is not effected by an absorption of the plugs with the adhesive.

21. A method for removing keratotic plugs using a dermatological patch comprising:

(a) applying to the skin of a user for a predetermined time a flexible pad, having adhered to its lower surface, a polymeric adhesive composition, the polymeric adhesive composition being sufficiently thick and continuous to adhere the patch with the skin and adhere the patch to keratotic plugs in the pores thereof, the polymeric adhesive composition not requiring the application of moisture to be effective in adhering to the skin or keratotic plugs, nor requiring the drying of the adhesive to effectively remove the keratotic plugs when the patch is removed from the skin; and (b) physically removing the dermatological patch upon the expiration of the time period, whereby the polymeric adhesive composition actively removes keratotic plugs from the pores by the adherence of the adhesive with the top of the keratotic plugs and a non-absorption of the plugs with the adhesive, such that the plugs are adhesively physically removed from the pores when the dermatological patch is physically removed from the skin.

22. The method of claim 21, where the polymeric adhesive composition is a pressure sensitive adhesive.

* * * * *